(12) United States Patent
Weber

(10) Patent No.: US 6,803,070 B2
(45) Date of Patent: Oct. 12, 2004

(54) APPARATUS AND METHOD FOR EMBEDDING NANOPARTICLES IN POLYMERIC MEDICAL DEVICES

(75) Inventor: Jan Weber, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/335,510

(22) Filed: Dec. 30, 2002

(65) Prior Publication Data

US 2004/0126481 A1 Jul. 1, 2004

(51) Int. Cl.[7] ................................................. B05D 1/04
(52) U.S. Cl. ..................... 427/2.24; 427/2.28; 427/475; 427/481; 427/483; 427/485
(58) Field of Search ................ 427/2.24–2.31, 427/523–528, 457–486; 361/226–228

(56) References Cited

U.S. PATENT DOCUMENTS

| | | | |
|---|---|---|---|
| 4,764,394 A | | 8/1988 | Conrad |
| 5,154,179 A | | 10/1992 | Ratner |
| 5,296,272 A | | 3/1994 | Matossian et al. |
| 5,693,376 A | | 12/1997 | Fetherston et al. |
| 5,744,958 A | | 4/1998 | Werne |
| 5,782,764 A | | 7/1998 | Werne |
| 6,030,371 A | * | 2/2000 | Pursley ........................ 604/527 |
| 6,040,019 A | | 3/2000 | Ishida et al. |
| 6,224,536 B1 | | 5/2001 | Pike |
| 6,294,223 B1 | | 9/2001 | Hampikian et al. |
| 6,361,759 B1 | | 3/2002 | Frayne et al. |
| 2002/0176822 A1 | | 11/2002 | Frayne et al. |
| 2003/0054090 A1 | * | 3/2003 | Hansen ........................ 427/2.1 |
| 2003/0143315 A1 | * | 7/2003 | Pui et al. ...................... 427/2.1 |
| 2004/0030377 A1 | * | 2/2004 | Dubson et al. ............ 623/1.13 |

OTHER PUBLICATIONS

En, et al., "*Plasma immersion ion implantation reactor design considerations for oxide charging,*" Journal of Surface & Coatings Technology, vol. 85, 1996, pp. 64–69.

Ishikawa, et al., "*Negative–Ion Implanter and Formation of Metal Nanoparticles in Glass,*" Proceedings of IIT2000, 4 pages, 2000.

Anders, "*Handbook of Plasma Immersion Ion Implantation and Deposition*" John Wiley & Sons, Inc., 2000.

Tan, et al., "*Biocompatibitlity Improvement of NiTi with a Functionally Graded Surface,*" Society for Experimental Mechanics, 2002 SEM Annual Conference Proceedings, 4 pages, 2002.

* cited by examiner

*Primary Examiner*—Fred J. Parker
(74) *Attorney, Agent, or Firm*—Marshall, Gerstein & Bourn LLP

(57) ABSTRACT

An apparatus and method for embedding particles into the polymer matrix of a medical device are disclosed. The apparatus may include an electrostatic spray nozzle adapted to direct a stream of nanoparticles dissolved in a solution toward a positive outlet. A medical device, mounted onto an electrode, can then be placed into or proximate the stream such that upon energization of the electrode, the charged particles are redirected from the outlet toward the electrode. By spacing the electrode and energizing the electrode appropriately, the charged particles can be accelerated to a degree sufficient to cause the charged particles to embed themselves into the polymer matrix of the medical device.

15 Claims, 3 Drawing Sheets

APPARATUS AND METHOD FOR EMBEDDING NANOPARTICLES IN POLYMERIC MEDICAL DEVICES

FIELD OF THE DISCLOSURE

Figure 1:
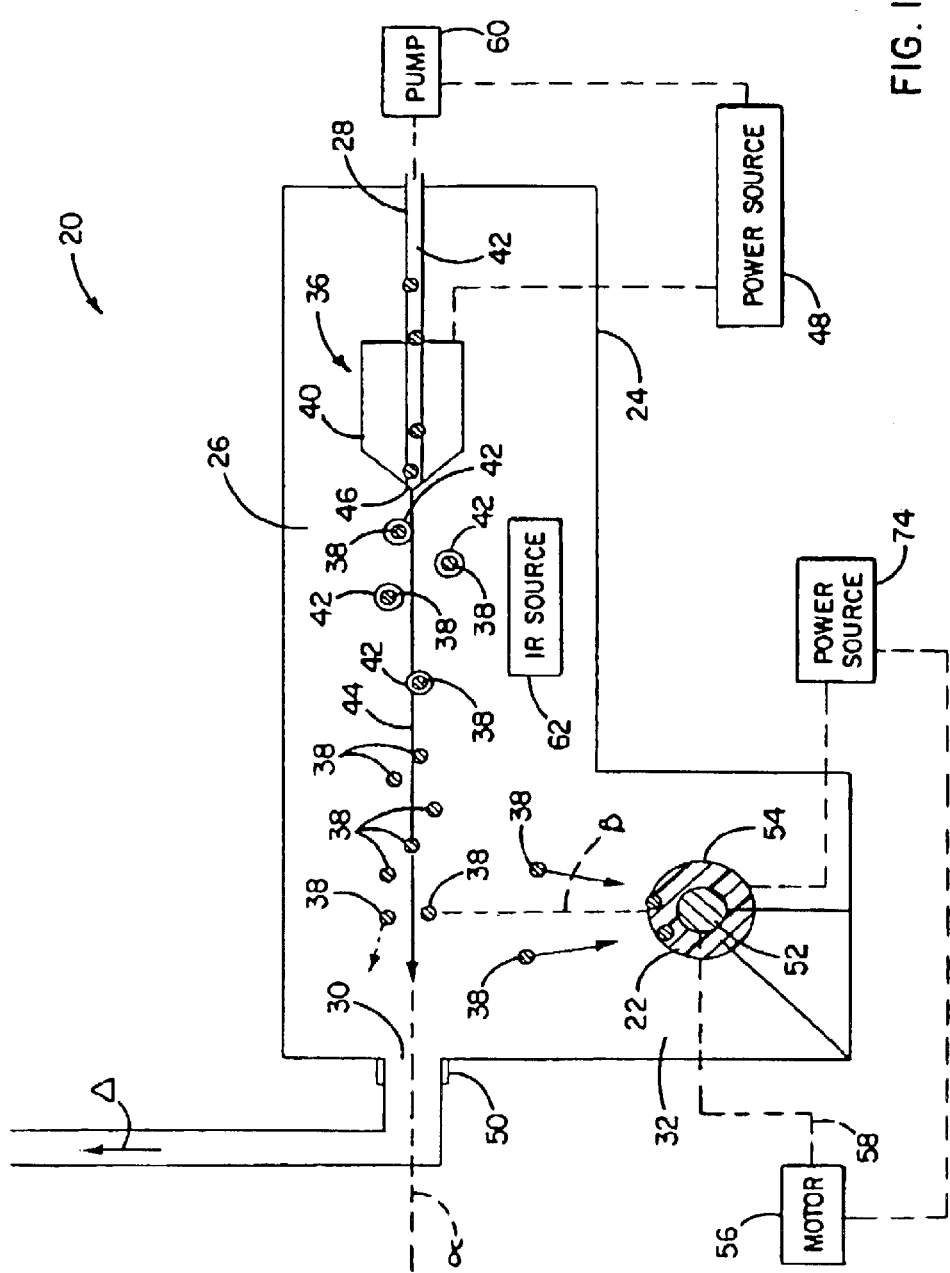

The disclosure generally relates to embedding particles into the polymer matrix of a medical device.

BACKGROUND OF THE DISCLOSURE

It is often desirable to embed or encapsulate nanometer-sized particles into the outer layer of medical devices. For example, super-paramagnetic particles can be placed within medical devices such as balloon catheters to thereby enhance the visibility of the device under magnetic resonance imaging (MRI). The super-paramagnetic particles disturb the local magnetic fields within the directly surrounding lumen in which the catheter is placed, and thereby become visible under MRI. Moreover, pharmaceuticals can be encapsulated within nanoparticles, which are then directed to a specific location within the body and released.

While it can therefore be seen that the incorporation of nanoparticles into medical devices has proven to be advantageous, current methods and apparatus for doing so are less than optimal. Currently, the dispersal of such nanoparticles through polymer matrices of medical devices is accomplished commonly through shear compounding. Such mechanical integration of the nanoparticles into the polymer matrix, however, typically is a relatively time-consuming, and thus costly process. Moreover, the forces involved negatively affect the quality of the polymer, and typically result in very poor dispersion of the particles throughout the device. In the event that pharmaceuticals are incorporated within the nanoparticles, such shear compounding also results in destruction of the pharmaceutical either due to the high resulting temperatures, or through the mechanical interaction.

It can therefore be seen that a need exists for an improved apparatus and method for incorporating nanoparticles into medical devices.

SUMMARY OF THE DISCLOSURE

In accordance with one aspect of the disclosure, a method of embedding nanoparticles into a medical device is disclosed which comprises forming a solution containing the nanoparticles, spraying the solution from a charged nozzle, evaporating the solution to form a stream of charged nanoparticles, energizing an electrode to have a polarity opposite to the charged nanoparticles thereby generating a stream of charged nanoparticles, and placing a medical device into the stream. The charged nanoparticles are thereby embedded into the medical device upon impact.

In accordance with another aspect of the disclosure an apparatus for embedding nanoparticles into a medical device, is disclosed which comprises a housing, an electrostatic spray nozzle, and an electrode. The housing may include an inlet, an outlet linearly opposed to the inlet, a pressure chamber between the inlet and the outlet, and an off-axis vacuum chamber between the inlet and the outlet in fluid communication with the pressure chamber. The electrode may be placed within the vacuum chamber and be adapted to have a medical device mounted thereon.

In accordance with another aspect of the disclosure, a method of treating a medical device is disclosed which may comprise generating a stream of charged particles, mounting a medical device about and an electrode charged oppositely to the particles, and spraying the charged particles toward the medical device.

In accordance with yet another aspect of the disclosure, an apparatus for treating medical devices is disclosed which may comprise a source of charged particles, an electrode charged oppositely to the charged particles, a stream of charged particles extending from the source to the electrode, and means for mounting a medical device in the stream.

These and other aspects and features of the disclosure will become more apparent upon reading the following detailed description when taken into consideration with the accompanying drawings.

BRIEF DESCRIPTION OF THE DRAWINGS

FIG. 1 is a schematic representation of an apparatus constructed in accordance with the teachings of the disclosure;

FIG. 2 is a flow chart depicting a sample sequence of steps which may be taken according to the teachings of the disclosure;

FIG. 3 is a graphical depiction of the energization sequence of the electrode of the apparatus of FIG. 1; and FIG. 4 is a side view of a medical device constructed in accordance with the teachings of the disclosure.

While the disclosure is susceptible to various modifications and alternative constructions, certain illustrative embodiments thereof have been shown in the drawings and will be described below in detail. It should be understood, however, that there is no intention to limit the disclosure to the specific examples disclosed, but on the contrary, the intention is to cover all modifications, alternative constructions, and the equivalents falling within the spirit and scope of the invention as defined by the appended claims.

DETAILED DESCRIPTION

Referring now to the drawings, and with specific reference to FIG. 1, an apparatus constructed in accordance with the teachings of the disclosure is generally referred to by reference numeral 20. While the following disclosure will be provided with reference to creating a medical device 22 in the form of a balloon catheter, it is to be understood that the apparatus 20 can be used with equal efficacy in constructing medical devices in addition to balloon catheters such as, but not limited to, other forms of catheters, syringes, introducer sheaths, stents, artificial joints, artificial organs, and filter wires.

Referring again to FIG. 1, the apparatus 20 may include a housing 24 defining a pressure chamber 26 having an inlet 28 and an outlet 30. The housing 24 may further include a vacuum chamber 32 in fluid communication with the pressure chamber 26. As will be noted from FIG. 1, the vacuum chamber 32 may be off-axis with respect to the pressure chamber 26 in that the inlet 28, 30 are linearly aligned along a longitudinal axis $\alpha$, with the vacuum chamber 32 not being therebetween, but rather being off to one side of the axis $\alpha$. It is to be understood that in alternative embodiments, the vacuum chamber 32 need not form the L-shape with respect to the pressure chamber 26 as depicted in FIG. 1, but can be provided in any other form of off-axis arrangement as well. It is advantageous to use a vacuum chamber to many other things, allow ions to be accelerated to high velocities without being bounced and slowed down by surrounding gas molecules.

Mounted within the housing 24, proximate the inlet 28, is a source 36 of charged particles 38. In the depicted embodiment, the source 36 is provided in the form of an electrostatic spray nozzle. The electrostatic spray nozzle includes an enclosure 40 adapted to receive a solution 42 and direct a stream 44 of charged particles 38 from a nozzle outlet 46. The enclosure 40 may be electrically connected to a power source 48 such as AC or DC power source or battery. In so doing, the particles 38 are ionized, e.g., negatively charged, upon passing through the nozzle 46.

The stream 44 generated by the nozzle 46 is directed toward the outlet 30 along the longitudinal axis α. The outlet 30 may be positively charged and include an electric isolator ring 50 so as to facilitate attraction of the charged particles 38 from the electrostatic spray gun 36 toward the outlet 30.

Disposed within the vacuum chamber 32 is an electrode 52 about which the medical device 22 may be mounted. While the outlet 30 is positively charged, and thus the charged particles 38 are attracted thereto, energization of the electrode 52 causes the charged particles 38 to be attracted thereto as well. Moreover, by spacing the electrode 52 away from the axis α a sufficient distance β, the charged particles 38 accelerate toward the electrode 52 and impact the medical device 22 with sufficient force so as to embed themselves into the polymer matrix of the medical device 22. Moreover by varying the distance β at which the electrode 52 is spaced, as well as the voltage applied to the electrode 52, the force with which the charged particles 38 impact the medical device 22 can be adjusted so as to penetrate the polymer matrix to varying degrees tailored to the end application for the medical device 22.

In order to ensure the charged particles 38 are embedded into the entire circumference 54 (when desired) of the medical device 22, the apparatus 20 may be further provided with a mechanism for rotating the electrode 52. This may be provided in the form of a motor 56 operatively associated with the electrode 52 by way of a connector 58. The connector 58 may be provided in any number of conventional mechanisms including, but not limited to, belts, gears, shafts, and the like.

In order to effectively spray the charged particles 38 from the electrostatic spray gun 36, it may prove to be advantageous to first dissolve nanoparticles, desired to be embedded into the medical device 22, into a suitable solvent. For example, if it is desired to embed super-paramagnetic particles, such as $Fe_2O_3$, $Fe_3O_4$, $CoFe_2O_4$, $MnFe_2O_4$, $MgFe_2O_4$ as well as any other nanocrystaline particle made of the transition metal oxides (Fe, Co, Ni) into a polyethylene polymer matrix of the medical device 22, the super-paramagnetic particles can be dissolved into a solvent, such as but not limited to, tolulene acetone, DMF, or any other solvent that allows for quick evaporation, to result in the solution 42. The solution 42 can then be sprayed as by a pump 60 through the nozzle 46 resulting in charged particles 38 accompanied by solution 42 as shown best in FIG. 1. Transportation of the charged particles 38 in solution 42 through the pressure chamber 26 causes the solution 42 to evaporate, and exit through the outlet 30 as indicated by arrow Δ leaving only the charged particles 38 for embedding into the medical device 22. In order to facilitate evaporation of the solution 42, any number of mechanisms for adding energy into the pressure chamber 26 can be provided. In the embodiment depicted in FIG. 1, an infrared radiation source 62 is mounted in the housing 24 proximate the nozzle 46.

Figure 3:
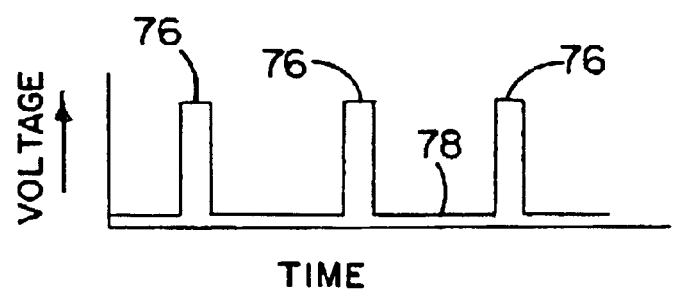
Figure 4:
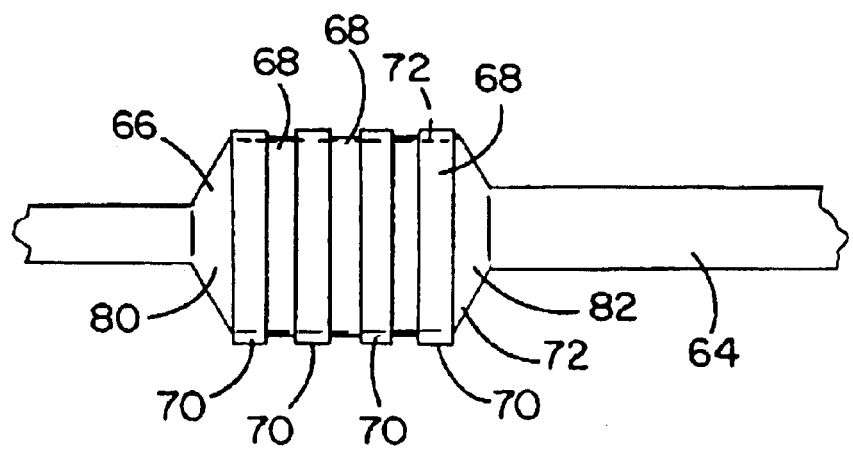

Turning now to FIGS. 3 and 4, an example of a medical device 22 constructed from the apparatus 20 of the present disclosure is shown in more detail. The medical device 22 depicted is provided in the form of a catheter 64 having a balloon section 66 formed therein. Moreover, it will be noted that a plurality of demarcation lines 68 or marker bands are formed in the balloon 66. Such bands 68 may prove to be advantageous in visualizing the balloon 66 once inserted into a lumen in that upon exposure to an MRI device, the marker band 68 will be readily apparent to the user to facilitate location of the balloon 66 within the lumen. The marker band 68 may be so formed by first masking the balloon 66 with a masking layer 70 in those areas where implantation of the charged particles 38 is not desired. Put another way, the masking layer 70 can be provided in the areas between the desired marker band 68. The masked balloon 66 can then be placed within the plasma chamber 32 as indicated above, and upon energization of the electrode 52, the charged particles 38 impact against the balloon 66 and embed themselves into both the polymer matrix of the medical device 22 and into the masking layer 70. However, after formation, the masking layer 70 can be removed to thereby provide a balloon 66 having marker bands 68 and clean areas 72 therebetween wherein the masking layer 70 was provided, and wherein charged particles 38 were prevented from becoming embedded into the polymer matrix of the medical device 22.

The electrode 52 may be connected to a power source 74, such as an AC or DC power source which can be modulated to provide the voltage wave depicted in FIG. 3. As shown therein, the voltage wave consists of a plurality of pulses 76 created by periods of low voltage 78. During each pulse 76, the electrode 52 is highly energized and thus attracts the charged particles 38 thereto, and during the periods of low voltage 78, the charged particles 38 are not attracted thereto, and thus exit through the outlet 30. However, the use of such a sine wave output, in conjunction with the motor 56, can result in the desired pattern being formed on the circumference 54 of the medical device 22. More specifically, the motor 56 causes the electrode 52 to rotate in an incremental fashion such that during each period of low voltage 78, the electrode 52 is rotated, for example, ninety degrees, to expose different sections of the medical device 22 circumference 54 to the charged particle 38 bombardment. After rotation, the electrode 52, and thus the medical device 22, stops whereupon the charged particles 38 are bombarded against, and embedded into, the medical device 22. Again, as indicated above, by varying the voltage of the AC power source 74, the force with which the charged particles 38 are imparted against the medical device 22 can be altered, and thus the distance to which the charged particles penetrate the polymer matrix of the medical device 22 can be varied. The device 22 could also be continuously rotated.

Moreover, the location of the electrode 52 within the medical device 22 can be altered in the event that it is desired for the charged particles 38 to embed themselves into only specific areas of the medical device 22. More specifically, with reference to FIG. 4, if the electrode 52 is mounted proximate a first end 80 of the balloon 66, the charged particles 38 will embed themselves proximate the first end 80 of the medical device 22 and not proximate a second end 82. Conversely, if the electrode 52 is mounted proximate a second end 82, the charged particles 38 will be attracted only to the second end 82 of the medical device 22.

Figure 2:
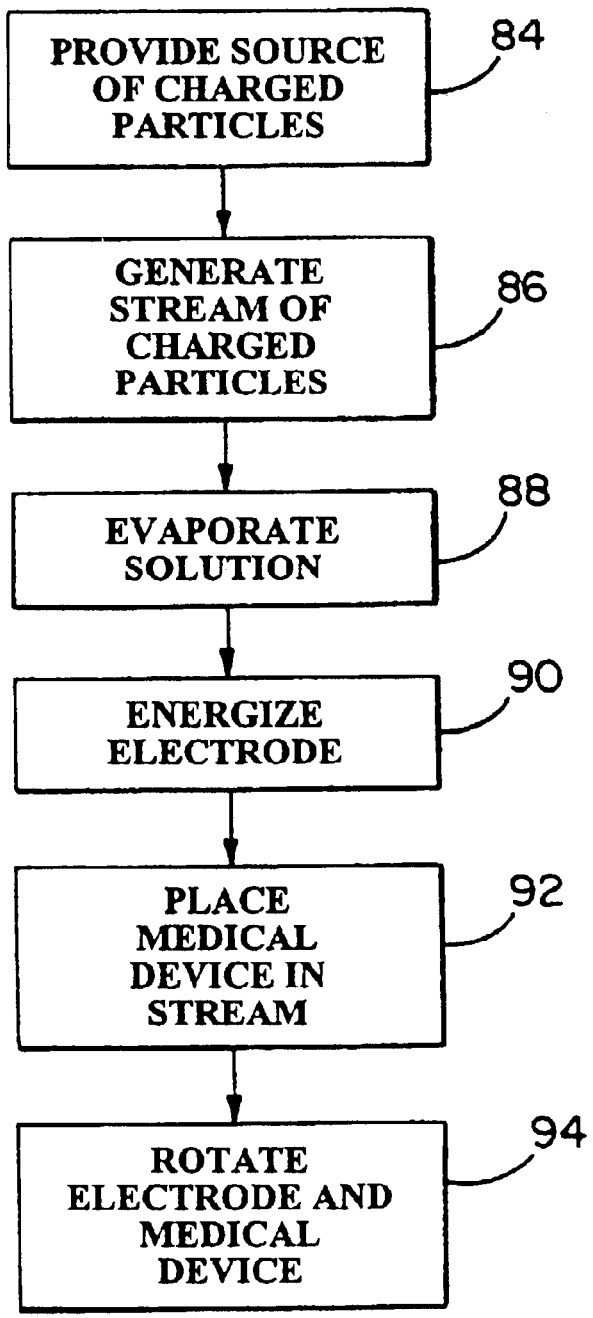

A sample sequence of steps which may be taken according to the teachings of the disclosure is depicted in flow chart format in FIG. 2. As shown therein, a first step 84 may be to provide a source of charged particles. As indicated above, this may be accomplished by forming the solution 42 of paramagnetic particles within a suitable solvent. Alternatively, the paramagnetic particles, or other particles, can be provided in powder form and simply blown across a charged member, such as a blade or the like.

Once the solution 42 is so formed, it can be directed through the electrostatic spray nozzle 46 to generate a stream of charged particles 38 and solution 42 as indicated in a step 86. The stream 44 is directed toward an oppositely charged outlet 30 and in so doing, the solution 42 is evaporated as indicated in a step 88, leaving only charged particles 38 within the pressure chamber 26. In a fourth step 90, the electrode 52 is energized intermittently, thereby causing the charged particles 38 to deflect away from the axis a and be accelerated toward the electrode 52. In a fifth step 92, the medical device 22 is placed within the stream 44 thereby causing the charged particles 38 to embed themselves via ion implantation into the polymer matrix of the medical device 22. As indicated above, this may be accomplished by mounting the medical device 22 onto the electrode 52 itself. However, it is to be understood that in alternative embodiments, the medical device 22 may be mounted into the stream 44 by any other means as well. In a sixth step 94, the electrode 52 and medical device 22 can be rotated so as to ensure the charged particles 38 are embedded into an entire circumference 54 of the medical device 22.

From the foregoing, one of ordinary skill in the art will appreciate that the teachings of the disclosure can be used to create an apparatus and method for embedding particles into medical devices.

What is claimed is:

1. A method of embedding nanoparticles into a medical device, comprising:

forming a solution containing the nanoparticles;

spraying the solution from a charged nozzle;

evaporating the solution to form a stream of charged nanoparticles along a first axis;

energizing an electrode to have a polarity opposite to the charged nanoparticles, a stream of charged nanoparticles along a second axis being thereby created, the second axis being transverse to the first axis; and placing a medical device in the stream along the second axis, the charged nanoparticles being embedded in the medical device upon impact.

2. A method of embedding nanoparticles into a medical device, comprising:

forming a solution containing the nanoparticles;

spraying the solution from a charged nozzle;

evaporating the solution to form a stream of charged nanoparticles along the first axis;

energizing an electrode to have a polarity opposite to the charged nanoparticles, a stream of charged nanoparticles along a second axis being thereby created; and placing a medical device in the stream along the second axis, the charged nanoparticles being embedded in the medical device upon impact, wherein the nanoparticles are super-paramagnetic particles.

3. The method of claim 2, wherein the super-paramagnetic particles are selected from the group consisting of $Fe_2O_3$, $Fe_3O_4$, $CoFe_2O_4$, $MnFe_2O_4$, and $MgFe_2O_4$.

4. A method of embedding nanoparticles into a medical device, comprising:

forming a solution containing the nanoparticles;

spraying the solution from a charged nozzle;

evaporating the solution to form a stream of charged nanoparticles along the first axis;

energizing an electrode to have a polarity opposite to the charged nanoparticles, a stream of charged nanoparticles along a second axis being thereby created; and placing a medical device in the stream along the second axis, the charged nanoparticles being embedded in the medical device upon impact, wherein the solution is evaporated using infrared radiation.

5. A method of embedding nanoparticles into a medical device, comprising:

forming a solution containing the nanoparticles;

spraying the solution from a charged nozzle;

evaporating the solution to form a stream of charged nanoparticles along the first axis;

energizing an electrode to have a polarity opposite to the charged nanoparticles, a stream of charged nanoparticles along a second axis being thereby created; and placing a medical device in the stream along the second axis, the charged nanoparticles being embedded in the medical device upon impact, wherein the electrode is positively charged, and the medical device is mounted around the electrode.

6. The method of claim 5, wherein the electrode and medical device are rotated while placed within the stream along the second axis.

7. The method of claim 6, wherein the medical device is masked in a predetermined pattern.

8. The method of claim 7, wherein the predetermined pattern is a series of spaced stripes.

9. A method of treating a medical device, comprising:

generating a stream of charged particles along a first axis;

mounting a medical device about an electrode charged oppositely to the particles, the medical device being positioned along a second axis transverse to the first axis; and energizing the electrode so as to redirect the stream of charged particles from the first axis to the second axis, thereby embedding charged particles in the medical device.

10. The method of claim 9, wherein the stream of charged particles is generated using an electrostatic spray nozzle.

11. A method of treating a medical device, comprising:

generating a stream of charged particles;

mounting a medical device about an electrode charged oppositely to the particles; and embedding charged particles in the medical device, wherein the stream of charged particles is generated by dissolving super-paramagnetic particles in a solvent and spraying the resulting solution through a negatively charged nozzle.

12. A method of treating a medical device, comprising:

generating a stream of charged particles;

mounting a medical device about an electrode charged oppositely to the particles; and embedding charged particles in the medical device, wherein the stream of charged particles is generated by blowing dry paramagnetic powder over a negatively charged blade.

13. The method of claim 9, wherein the medical device is manufactured from a polymer.

14. The method of claim 9, further including rotating the medical device while spraying.

15. A method of treating a medical device, comprising:

generating a stream of charged particles;

mounting a medical device about an electrode charged oppositely to the particles; and embedding charged particles in the medical device, further including masking the medical device in a predetermined pattern prior to spraying.

* * * * *